(12) United States Patent
Powell et al.

(10) Patent No.: US 6,319,689 B1
(45) Date of Patent: Nov. 20, 2001

(54) ASP2

(75) Inventors: David J Powell, Radnor, PA (US); Conrad G Chapman, Orpington; Kay Murphy, Herts, both of (GB); Trudi S Smith, Radnor, PA (US)

(73) Assignees: SmithKline Beecham Corporation, Philadelphia, PA (US); SmithKline Beecham plc, Brentford (GB)

( * ) Notice: Subject to any disclaimer, the term of this patent is extended or adjusted under 35 U.S.C. 154(b) by 0 days.

(21) Appl. No.: 09/009,191

(22) Filed: Jan. 20, 1998

(30) Foreign Application Priority Data

Jan. 28, 1997 (GB) .................................................. 9701684

(51) Int. Cl.[7] .......................... C12P 21/06; C12N 15/09; C12N 1/20; C12N 15/00; C07H 21/02
(52) U.S. Cl. .................. 435/69.1; 435/252.3; 435/320.1; 435/70.1; 435/71.1; 536/23.1
(58) Field of Search .................................. 435/69.1, 70.1, 435/71.1, 71.2, 325, 252.3, 254.11, 320.1, 471, 476, 483; 536/23.2, 23.7

(56) References Cited

FOREIGN PATENT DOCUMENTS

0848062 A * 6/1998 (EP) .
0855444 A * 7/1998 (EP) .
WO9510630 * 4/1995 (WO) .

OTHER PUBLICATIONS

Vassar et al., Science 286(5440):735–41, Oct. 22, 1999.*
Miyata et al, Br J of Haematology, 1994, 88, 156–65.*
GenEmbl Accession G24698, human STS WI–14206, 1996.*
GenEmbl Accession MFPEPA4, M. fuscata mRNA for pepsinogen A–4, 1991.*
O'Toole et al., Mol. Microbiol., 14(4):691–703, 1994.*
Taylor et al., J. of Bacteriol., 174(21):6800–06, 1992.*
Skolnick et al., Trends in Biotech., 18(1):34–39, 2000.*
Human Genome Sciences Corporation EST # 716238.
Human Genome Sciences Corporation EST # 1445580.
Mori, et al., "Molecular cloning of a novel mouse aspartic protease–like protein that is expressed abundantly in the kidney", FEBS Letters, vol. 401, pp. 218–222 (1997).

* cited by examiner

Primary Examiner—Christine J. Saoud
Assistant Examiner—Sharon Turner
(74) Attorney, Agent, or Firm—William T. Han; Ratner & Prestia; William T. King

(57) ABSTRACT

ASP2 polypeptides and polynucleotides and methods for producing such polypeptides by recombinant techniques are disclosed. Also disclosed are methods for utilizing ASP2 polypeptides and polynucleotides in the design of protocols for the treatment of Alzheimer's Disease, cancer, and prohormone processing, among others, and diagnostic assays for such conditions.

11 Claims, No Drawings

ASP2

This application claims the benefit of U.K. Application No. 9701684.4, filed Jan. 28, 1997, which is herein incorporated by reference in its entirety.

FIELD OF INVENTION

This invention relates to newly identified polynucleotides, polypeptides encoded by them and to the use of such polynucleotides and polypeptides, and to their production. More particularly, the polynucleotides and polypeptides of the present invention relate to Aspartic Proteinase family, hereinafter referred to as ASP2. The invention also relates to inhibiting or activating the action of such polynucleotides and polypeptides.

BACKGROUND OF THE INVENTION

There are currently five known human aspartic proteases, namely, pepsin, gastricsin, cathespin D, cathespin E and renin, and these have widely varying functions. Pepsin and gastricsin are involved in nutritive processes in the stomach, cathepsin D is involved in protein turnover in many cell types, and renin has the highly specific function of angiotensin production from its precursor form, angiotensinogen. The precise role of cathepsin E remains to be confirmed, although its location in some epithelial cells types has indicated a role in antigen processing. It may also be involved in certain inflammatory conditions, such as *Helicobacter pylori* infection in the stomach. This indicates that the Aspartic Proteinase family has an established, proven history as therapeutic targets. Clearly there is a need for identification and characterization of further members of Aspartic Proteinase family which can play a role in preventing, ameliorating or correcting dysfunctions or diseases, including, but not limited to, Alzheimer's Disease, cancer, and prohormone processing.

SUMMARY OF THE INVENTION

In one aspect, the invention relates to ASP2 polypeptides and recombinant materials and methods for their production. Another aspect of the invention relates to methods for using such ASP2 polypeptides and polynucleotides. Such uses include the treatment of Alzheimer's Disease, cancer, and prohormone processing, among others. In still another aspect, the invention relates to methods to identify agonists and antagonists using the materials provided by the invention, and treating conditions associated with ASP2 imbalance with the identified compounds. Yet another aspect of the invention relates to diagnostic assays for detecting diseases associated with inappropriate ASP2 activity or levels.

DESCRIPTION OF THE INVENTION

Definitions

The following definitions are provided to facilitate understanding of certain terms used frequently herein.

"ASP2" refers, among others, generally to a polypeptide having the amino acid sequence set forth in SEQ ID NO:2 or an allelic variant thereof "ASP2 activity or ASP2 polypeptide activity" or "biological activity of the ASP2 or ASP2 polypeptide" refers to the metabolic or physiologic function of said ASP2 including similar activities or improved activities or these activities with decreased undesirable side-effects. Also included are antigenic and immunogenic activities of said ASP2.

"ASP2 gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydcoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which arc well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Post-translational Protein Modifications: Perspectives and Prospects, pgs. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzymol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not Known to occur naturally. Non-naturally occurring variants of polynucleotides and polypeptides may be made by mutagenesis techniques or by direct synthesis.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; *and Sequence Analysis Primer*, Gribskov, M. and Devereux, J., eds., M Stockton Press, New York, 1991; and Carillo, H., and Lipman, D., SIAM J. *Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215. 403–410 (1990). The BLAST X program is publicly available from NCBI and other sources (*BLAST Manual,* Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Preferred parameters for polypeptide sequence comparison include the following:
1) Algorithm: Needleman and Wunsch, J. Mol Biol. 48: 443–453 (1970)
Comparison matrix: BLOSSUM62 from Hentikoff and Hentikoff, Proc. Natl. Acad. Sci. USA. 89:10915–10919 (1992)
Gap Penalty: 12
Gap Length Penalty: 4

A program useful with these parameters is publicly available as the "gap" program from Genetics Computer Group, Madison Wis. The aforementioned parameters are the default parameters for polypeptide comparisons (along with no penalty for end gaps).

Preferred parameters for polynucleotide comparison include the following:
1) Algorithm: Needleman and Wunsch, J. Mol Biol. 48: 443–453 (1970)
Comparison matrix: matches=+10, mismatch=0
Gap Penalty: 50
Gap Length Penalty: 3

A program useful with these parameters is publicly available as the "gap" program from Genetics Computer Group, Madison Wis. The aforementioned parameters are the default parameters for polynucleotide comparisons.

Preferred polynucleotide embodiments further include an isolated polynucleotide comprising a polynucleotide having at least a 50,60, 70, 80, 85, 90, 95, 97 or 100% identity to a polynucleotide reference sequence of SEQ ID NO:1, wherein said reference sequence may be identical to the sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the numerical percent of the respective percent identity and subtracting that product from said total number of nucleotides in SEQ ID NO:1, or:

$$n_n \leq x_n - (x_n \cdot y),$$

wherein $n_n$ is the number of nucleotide alterations, Xn is the total number of nucleotides in SEQ ID NO:1, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frame-shift mutations in this coding sequence and thereby alter the polypeptide encoded by the polynucleotide following such alterations.

Preferred polypeptide embodiments further include an isolated polypeptide comprising a polypeptide having at least a 50,60, 70, 80, 85, 90, 95, 97 or 100% identity to a polypeptide reference sequence of SEQ ID NO:2, wherein said reference sequence may be identical to the sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the numerical percent of the respective percent identity and subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of $x_a$ and y is rounded down to the nearest integer prior to subtracting it from $x_a$.

Polypeptides of the Invention

In one aspect, the present invention relates to ASP2 polypeptides (or ASP2 proteins). The ASP2 polypeptides include the polypeptide of SEQ ID NOS:2 and 4; as well as polypeptides comprising the amino acid sequence of SEQ ID NO: 2; and polypeptides comprising the amino acid sequence which have at least 80% identity to that of SEQ ID NO:2 over its entire length, and still more preferably at least 90% identity, and even still more preferably at least 95% identity to SEQ ID NO: 2. Furthermore, those with at least 97–99% are highly preferred. Also included within ASP2 polypeptides are polypeptides having the amino acid sequence which have at least 80% identity to the polypeptide having the amino acid sequence of SEQ ID NO:2 over its entire length, and still more preferably at least 90% identity, and still more preferably at least 95% identity to SEQ ID NO:2. Furthermore, those with at least 97–99% are highly preferred. Preferably ASP2 polypeptide exhibit at least one biological activity of ASP2.

The ASP2 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Fragments of the ASP2 polypeptides are also included in the invention. A fragment is a polypeptide having an amino acid sequence that entirely is the same as part, but not all, of the amino acid sequence of the aforementioned ASP2 polypeptides. As with ASP2 polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end ASP2 polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of ASP2 polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate ASP2 activity, including those with a similar activity or an improved activity, or with a decreased undesirable activity. Also included are those that are antigenic or immunogenic in an animal, especially in a human.

Preferably, all of these polypeptide fragments retain the biological activity of the ASP2, including antigenic activity. Among the most preferred fragment is that having the amino acid sequence of SEQ ID NO: 4. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The ASP2 polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to ASP2 polynucleotides. ASP2 polynucleotides include isolated polynucleotides which encode the ASP2 polypeptides and fragments, and polynucleotides closely related thereto. More specifically, ASP2 polynucleotide of the invention include a polynucleotide comprising the nucleotide sequence contained in SEQ ID NO:1 encoding a ASP2 polypeptide of SEQ ID NO: 2, and polynucleotides having the particular sequences of SEQ ID NOS:1 and 3. ASP2 polynucleotides further include a polynucleotide comprising a nucleotide sequence that has at least 80% identity over its entire length to a nucleotide sequence encoding the ASP2 polypeptide of SEQ ID NO:2, and a polynucleotide comprising a nucleotide sequence that is at least 80% identical to that of SEQ ID NO:1 over its entire length. In this regard, polynucleotides at least 90% identical are particularly preferred, and those with at least 95% are especially preferred. Furthermore, those with at least 97% arc highly preferred and those with at least 98–99% are most highly preferred, with at least 99% being the most preferred. Also included under ASP2 polynucleotides are a nucleotide sequence which has sufficient identity to a nucleotide sequence contained in SEQ ID NO:1 to hybridize under conditions useable for amplification or for use as a probe or marker. The invention also provides polynucleotides which are complementary to such ASP2 polynucleotides.

ASP2 of the invention is structurally related to other proteins of the Aspartic Proteinase family, as shown by the results of sequencing the cDNA encoding human ASP2. The cDNA sequence of SEQ ID NO:1 contains an open reading frame (nucleotide number 1 to 1503) encoding a polypeptide of 501 amino acids of SEQ ID NO:2. The anmino acid sequence of Table 1 (SEQ ID NO:2) has about 48.7% identity (using FASTA (GCG)) in 460 amino acid residues with ASP1, Novel Aspartic Proteinase, (U.S. Pat. No. 6,025, 180. The nucleotide sequence of Table 1 (SEQ ID NO:1) has about 59.2% identity (using FASTA (GCG)) in 1516 nucleotide residues with ASP1 Novel Aspartic Proteinase (U.S. Pat. No. 6,025,180). Thus, ASP2 polypeptides and polynucleotides of the present invention are expected to have, inter alia, similar biological functions/properties to their homologous polypeptides and polynucleotides, and their utility is obvious to anyone skilled in the art.

TABLE 1[a]

ATGGCCCAAGCCCTGCCCTGGCTCCTGCTGTGGATGGGCGCGGGAGTGCTGCCTGCCCACGGCACCCAG

CACGGCATCCGGCTGCCCCTGCGCAGCGGCCTGGGGGGCGCCCCCCTGGGGCTGCGGCTGCCCCGGGAG

ACCGACGAAGAGCCCGAGGAGCCCGGCCGGAGGGGCAGCTTTGTGGAGATGGTGGACAACCTGAGGGGC

AAGTCGGGGCAGGGCTACTACGTGGAGATGACCGTGGGCAGCCCCCCGCAGACGCTCAACATCCTGGTG

GATACAGGCAGCAGTAACTTTGCAGTGGGTGCTGCCCCCCACCCCTTCCTGCATCGCTACTACCAGAGG

CAGCTGTCCAGCACATACCGGGACCTCCGGAAGGGTGTGTATGAGCCCTACACCCAGGGCAAGTGGGAA

GGGGAGCTGGGCACCGACCTGGTAAGCATCCCCCATGGCCCCAACGTCACTGTGCGTGCCAACATTGCT

GCCATCACTGAATCAGACAAGTTCTTCATCAACGGCTCCAACTGGGAAGGCATCCTGGGGCTGGCCTAT

GCTGAGATTGCCAGGCCTGACGACTCCCTGGAGCCTTTCTTTGACTCTCTGGTAAAGCAGACCCACGTT

CCCAACCTCTTCTCCCTGCAGCTTTGTGGTGCTGGCTTCCCCCTCAACCAGTCTGAAGTGCTGGCCTCT

GTCGGAGGGAGCATGATCATTGGAGGTATCGACCACTCGCTGTACACAGGCAGTCTCTGGTATACACCC

ATCCGGCGGGAGTGGTATTATGAGGTGATCATTGTGCGGGTGGAGATCAATGGACAGGATCTGAAAATG

GACTGCAAGGAGTACAACTATGACAAGAGCATTGTGGACAGTGGCACCACCAACCTTCGTTTGCCCAAG

AAAGTGTTTGAAGCTGCAGTCAAATCCATCAAGGCAGCCTCCTCCACGGAGAAGTTCCCTGATGGTTTC

TGGCTAGGAGAGCAGCTGGTGTGCTGGCAAGCAGGCACCACCCCTTGGAACATTTTCCCAGTCATCTCA

CTCTACCTAATGGGTGAGGTTACCAACCAGTCCTTCCGCATCACCATCCTTCCGCAGCAATACCTGCGG

CCAGTGGAAGATGTGGCCACGTCCCAAGACGACTGTTACAAGTTTGCCATCTCACAGTCATCCACGGGC

ACTGTTATGGGAGCTGTTATCATGGAGGGCTTCTACGTTGTCTTTGATCGGGCCCGAAAACGAATTGGC

TTTGCTGTCAGCGCTTGCCATGTGCACGATGAGTTCAGGACGGCAGCGGTGGAAGGCCCTTTTGTCACC

TTGGACATGGAAGACTGTGGCTACAACATTCCACAGACAGATGAGTCAACCCTCATGACCATAGCCTAT

GTCATGGCTGCCATCTGCGCCCTCTTCATGCTGCCACTCTGCCTCATGGTGTGTCAGTGGCGCTGCCTC

CGCTGCCTGCGCCAGCAGCATGATGACTTTGCTGATGACATCTCCCTGCTGAAGTGAGGAGGCCCATGG

GAGAAAGATAGAGATTCCCCTGGGACCACACCTCCGTGGTTCACTTTGGTCACAAGTAGGAGACACAGA

TGGCACCTGTGGCCAGAGCACCTCAGGACCCTCCCCACCCACCAAATGCCTCTGCCTTGATGGAGAAGG

AAAAGGCTGGCAAGGTGGGTTCCAGGGACTGTACCTGTAGGAAACAGAAAAGAGAAGAAAGAAGCACTC

TGCTGGCGGGAATACTCTTGGTCACCTCAAATTTAAGTCGGGAAATTCTGCTGCTTGAAACTTCAGCCC

TGAACCTTTGTCCACCATTCCTTTAAATTCTCCAACCCAAAGTATTCTTCTTTTCTTAGTTTCAGAAGT

ACTGGCATCACACGCAGGTTACCTTGGCGTGTGTCCCTGTGGTACCCGGGCAGAGAAGAGACCAAGCTT

GTTTCCCTGCTGGGCCAAAGTCAGTAGGAGAGGATGCACAGTTTGCTATTTGCTTTAGAGACAGGGACT

GTATAAACAAGCCTAACATTGGTGCAAAGATTGCCTCTTGAATTAAAAAAAAAAAATAGATTGACTATT

TATACAAATGGGGCGGCTGGAAAGAGGAGAAGGAGAGGGAGTACAAAGACAGGGAATAGTGGGATCAA

AGCTAGGAAAGGCAGAAACACAACCACTCACCAGTCCTAGTTTTAGACCTCATCTCCAAGATAGCATCC

CATCTCAGAAGATGGGTGTTGTTTTCAATGTTTTCTTTTCTGTGGTTGCAGCCTGACCAAAAGTGAGAT

TABLE 1ª-continued

```
GGGAAGGGCTTATCTAGCCAAAGAGCTCTTTTTTAGCTCTCTTAAATGAAGTGCCCACTAAGGAAGTTC

CACTTGAACACATGGAATTTCTGCCATATTAATTTCCATTGTCTCTATCTGGAACCACCCTTTAATCTC

TACATATGATTAGGTCCAGCACTTGAAAATATTCCTAACCNNAATTTGNCTTGGGGGCTTTGCNGN

CCAGGTGCTAAAAGGGNTTGGGTAGGNGNCCNCTTNTATNTNATNCCTNAAAAGGTTANNG
```

ªA nucleotide sequence of a human ASP2 (SEQ ID NO:1).

TABLE 2ᵇ

```
MAQALPWLLLWMGAGVLPAHGTQHGIRLPLRSGLGGAPLGLRLPRETDEEPEEPGRRGSFVEMVDNLRG

KSGQGYYVEMTVGSPPQTLNILVDTGSSNFAVGAAPHPFLHRYYQRQLSSTYRDLRKGVYEPYTQGKWE

GELGTDLVSIPHGPNVTVRANIAAITESDKFFINGSNWEGILGLAYAEIARPDDSLEPFFDSLVKQTHV

PNLFSLQLCGAGFPLNQSEVLASVGGSMIIGGIDHSLYTGSLWYTPIRREWYYEVIIVRVEINGQDLKM

DCKEYNYDKSIVDSGTTNLRLPKKVFEAAVKSIKAASSTEKFPDGFWLGEQLVCWQAGTTPWNIFPVIS

LYLMGEVTNQSFRITILPQQYLPPVEDVATSQDDCYKFAISQSSTGTVMGAVIMEGFYVVFDRARKRIG

FAVSACHVHDEFRTAAVEGPFVTLDMEDCGYNIPQTDESTLMTIAYVMAAICALFMLPLCLMVCQWRCL

RCLRQQHDDFADDISLLK
```

ᵇAn amino acid sequence of a human ASP2 (SEQ ID NO: 2).

One polynucleotide of the present invention encoding ASP2 may be obtained using standard cloning and screening, from a cDNA library derived from mRNA in cells of human pancreas and brain, using the expressed sequence tag (EST) analysis (Adams, M. D., et al. *Science* (1991) 252:1651–1656; Adams, M. D. et al., *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding ASP2 polypeptide of SEQ ID NO:2 may be identical to the polypeptide encoding sequence contained in Table 1 (nucleotide number 1 to 1503 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of ASP2 polypeptide, the polynucleotide may include the coding sequence for the mature polypeptide or a fragment thereof, by itself, the coding sequence for the mature polypeptide or fragment in reading frame with other coding sequences, such as those encoding a leader or secretory sequence, a pre-, or pro- or preproprotein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al., *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding ASP2 variants comprising the amino acid sequence of ASP2 polypeptide of Table 2 (SEQ ID NO:2) in which several, 5–10, 1–5, 1–3, 1–2 or 1 amino acid residues are substituted, deleted or added, in any combination. Among the preferred polynucleotides of the present invention is contained in Table 3 (SEQ ID NO: 3) encoding the amino acid sequence of Table 4 (SEQ ID NO: 4).

TABLE 3ᶜ

```
GGCAGCTTTGTGGAGATGGTGGACAACCTGAGGGGCAAGTCGGGGCAGGGCTACTACGTGGAGATGACC

GTGGGCAGCCCCCCGCAGACGCTCAACATCCTGGTGGATACAGGCAGCAGTAACTTTGCAGTGGGTGCT

GCCCCCCACCCCTTCCTGCATCGCTACTACCAGAGGCAGCTGTCCAGCACATACCGGGACCTCCGGAAG

GGTGTGTATGAGCCCTACACCCAGGGCAAGTGGGAAGGGAGCTGGGCACCGACCTGGTAAGCATCCCC

CATGGCCCCAACGTCACTGTGCGTGCCAACATTGCTGCCATCACTGAATCAGACAAGTTCTTCATCAAC

GGCTCCAACTGGGAAGGCATCCTGGGGCTGGCCTATGCTGAGATTGCCAGGCCTGACGACTCCCTGGAG
```

TABLE 3[c]-continued

```
CCTTTCTTTGACTCTCTGGTAAAGCAGACCCACGTTCCCAACCTCTTCTCCCTGCAGCTTTGTGGTGCT

GGCTTCCCCCTCAACCAGTCTGAAGTGCTGGCCTCTGTCGGAGGGAGCATGATCATTGGAGGTATCGAC

CACTCGCTGTACACAGGCAGTCTCTGGTATACACCCATCCGGCGGGAGTGGTATTATGAGGTGATCATT

GTGCGGGTGGAGATCAATGGACAGGATCTGAAAATGGACTGCAAGGAGTACAACTATGACAAGAGCATT

GTGGACAGTGGCACCACCAACCTTCGTTTGCCCAAGAAAGTGTTTGAAGCTGCAGTCAAATCCATCAAG

GCAGCCTCTCCACGGGAGAAGTTCCCTGATGGTTTCTGGCTAGGAGAGCAGCTGGTGTGCTGGCAAGCA

GGCACCACCCCTTGGAACATTTTCCCAGTCATCTCACTCTACCTAATGGGTGAGGTTACCAACCAGTCC

TTCCGCATCACCATCCTTCCGCAGCAATACCTGCGGCCAGTGGAAGATGTGGCCACGTCCCAAGACGAC

TGTTACAAGTTTGCCATCTCACAGTCATCCACGGGCACTGTTATGGGAGCTGTTATCATGGAGGGCTTC

TACGTTGTCTTTGATCGGGCCCGAAAACGAATTGGCTTTGCTGTCAGCGCTTGCCATGTGCACGATGAG

TTCAGGACGGCAGCGGTGGAAGGCCCTTTTGTCACCTTGGACATGGAAGACTGTGGCTACAACATTCCA

CAGACAGATGAGTCAACCCTCATGACCATAGCCTATGTCATGGCTGCCATCTGCGCCCTCTTCATGCTG

CCACTCTGCCTCATGGTGTGTCAGTGGCGCTGCCTCCGCTGCCTGCGCCAGACAATGGATGACTTTGCT

GATGACATCTCCCTGCTGAAGTGAGGAGGCCCATGGGAGAAAGATAGAGATTCCCCTGGGACCACACCT

CCGTGGTTCACTTTGGTCACAAGTAGGAGACACAGATGGCACCTGTGGCCAGAGCACCTCAGGACCCTC

CCCACCCACCAAATGCCTCTGCCTTGATGGAGAAGGAAAAGGCTGGCAAGGTGGGTTCCAGGGACTGTA

CCTGTAGGAAACAGAAAAGAGAAGAAAGAAGCACTCTGCTGGCGGGAATACTCTTGGTCACCTCAAATT

TAAGTCGGGAAATTCTGCTGCTTGAAACTTCAGCCCTGAACCTTTGTCCACCATTCCTTTAAATTCTCC

AACCCAAAGTATTCTTCTTTTCTTAGTTTCAGAAGTACTGGCATCACACGCAGGTTACCTTGGCGTGTG

TCCCTGTGGTACCCGGGCAGAGAAGAGACCAAGCTTGTTTCCCTGCTGGCCAAAGTCAGTAGGAGAGGA

TGCACAGTTTGCTATTTGCTTTAGAGACAGGGACTGTATAAACAAGCCTAACATTGGTGCAAAGATTGC

CTCTTGAATTAAAAAAAAAAACTAGATTGACTATTTATACAAATGGGGCGGCTGGAAAGAGGAGAAGG

AGAGGGAGTACAAAGACAGGGAATAGTGGGATCAAAGCTAGGAAAGGCAGAAACACAACCACTCACCAG

TCCTAGTTTTAGACCTCATCTCCAAGATAGCATCCCATCTCAGAAGATGGGTGTTGTTTTCAATGTTTT

CTTTTCTGTGGTTGCAGCCTGACCAAAAGTGAGATGGGAAGGGCTTATCTAGCCAAAGAGCTCTTTTTT

AGCTCTCTTAAATGAAGTGCCCACTAAGGAAGTTCCACTTGAACACATGGAATTTCTGCCATATTAATT

TCCATTGTCTCTATCTGGAACCACCCTTTAATCTCTACATATGATTAGGTCCAGCACTTGAAAATATTC

CTAACCNNAATTTGNCTTGGGGGCTTTGCNGNCCAGGTGCTAAAAGGGNTTGGGTAGGNGNCCNCTTNT

ATNTNATNCCTNAAAAGGTTANNG
```

[c]A partial nucleotide sequence of a human ASP2 (SEQ ID NO: 3).

TABLE 4[d]

```
GSFVEMVDNLRGKSGQGYYVEMTVGSPPQTLNILVDTGSSNFAVGAAPHPFLHRYYQRQLSSTYRDLRK

GVYEPYTQGKWEGELGTDLVSIPHGPNVTVRANIAAITESDKFFINGSNWEGILGLAYAEIARPDDSLE

PFFDSLVKQTHVPNLFSLQLCGAGFPLNQSEVLASVGGSMIIGGIDHSLYTGSLWYTPIRREWYYEVII

VRVEINGQDLKMDCKEYNYDKSIVDSGTTNLRLPKKVFEAAVKSIKAASPREKFPDGFWLGEQLVCWQA

GTTPWNIFPVISLYLMGEVTNQSFRITILPQQYLRPVEDVATSQDDCYKFAISQSSTGTVMGAVIMEGF

YVVFDRARKRIGFAVSACHVHDEFRTAAVEGPFVTLDMEDCGYNIPQTDESTLMTIAYAMAAICALFML
```

TABLE 4[d]-continued

```
PLCLMVCQWRCLRCLRQTMDDFADDISLLK.GGPWEKDRDSPGTTPPWFTLVTSRRHRWHLWPEHLRTL

PTHQMPLP.WRRKRLARWVPGTVPVGNRKEKKEALCWREYSWSPQI.VGKFCCLKLQP.TFVHHSFKFS

NPKYSSFLSFRSTGITRRLPWRVSLWYPGREETKLVSLLAKVSRRGCTVCYLL.RQGLYKQA.HWCKDC

LLN.KKKLD.LFIQMGAAGKRRRRGSTKTGNSGIKARKGRNTTTHQS.F.TSSPR.HPISEDGCCFQCF

LFCGCSLTKSEMGRAYLAKELFFSSLK.SAH.GSST.THGISAILISIVSIWNHPLISTYD.VQHLKIF

LTXIXLGGFAXQVLKGXG.XXXXXXXLKRLX
```

[d]A partial amino acid sequence of a human ASP2 (SEQ ID NO: 4).

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97-99% identity between the sequences.

Polynucleotides of the invention, which are identical or sufficiently identical to a nucleotide sequence contained in SEQ ID NO:1 or a fragment thereof (including that of SEQ ID NO:3), may be used as hybridization probes for cDNA and genomic DNA, to isolate full-length cDNAs and genomic clones encoding ASP2 polypeptide and to isolate cDNA and genomic clones of other genes (including genes encoding homologs and orthologs from species other than human) that have a high sequence similarity to the ASP2 gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding ASP2 polypeptide, including homologs and orthologs from species other than human, comprises the steps of screening an appropriate library under stingent hybridization conditions with a labeled probe having the SEQ ID NO: 1 or a fragment thereof (including that of SEQ ID NO: 3), and isolating full-length cDNA and genomic clones containing said polynucleotide sequence. Such hybridization techniques are well known to those of skill in the art. Thus in another aspect, ASP2 polynucleotides of the present invention further include a nucleotide sequence comprising a nucleotide sequence that hybridize under stringent condition to a nucleotide sequence having SEQ ID NO: 1 or a fragment thereof (including that of SEQ ID NO:3). Also included with ASP2 polypeptides are polypeptide comprising amnino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH7.6), 5×Denhardt'ssolution, 10 % dextran sulfate, and 20 microgram/mi denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transfection, microinjection, cationic lipid-mediated transfection, electroporation, transduction, scrape loading, ballistic introduction or infection.

Representative examples of appropriate hosts include bacterial cells, such as streptococci, staphylococci, E. coli, Streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposes, from yeast episodes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the ASP2 polypeptide is to be expressed for use in screening assays, generally, it is preferred that the polypeptide be produced at the surface of the cell. In this event, the cells may be harvested prior to use in the screening assay. If ASP2 polypeptide is secreted into the medium, the medium can be recovered in order to recover and purify the polypeptide; if produced intracellularly, the cells must first be lysed before the polypeptide is recovered. ASP2 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of ASP2 polynucleotides for use as diagnostic reagents. Detection of a mutated form of ASP2 gene associated with a dysfunction will provide a diagnostic tool that can add to or define a diagnosis of a disease or susceptibility to a disease which results from under-expression, over-expression or altered expression of ASP2. Individuals carrying mutations in the ASP2 gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled ASP2 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science,* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397–4401. In another embodiment, an array of oligonucleotides probes comprising ASP2 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science,* Vol 274, pp 610–613 (1996)).

The diagnostic assays offer a process for diagnosing or determining a susceptibility to Alzheimer's Disease, cancer, and prohormone processing through detection of mutation in the ASP2 gene by the methods described.

In addition, Alzheimer's Disease, cancer, and prohormone processing, can be diagnosed by methods comprising determining from a sample derived from a subject an abnormally decreased or increased level of ASP2 polypeptide or ASP2 mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an ASP2 polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly Alzheimer's Disease, cancer, and prohormone processing, which comprises:
(a) a ASP2 polynucleotide, preferably the nucleotide sequence of SEQ ID NO: 1, or a fragment thereof;
(b) a nucleotide sequence complementary to that of (a);
(c) a ASP2 polypeptide, preferably the polypeptide of SEQ ID NO: 2, or a fragment thereof; or
(d) an antibody to a ASP2 polypeptide, preferably to the polypeptide of SEQ ID NO: 2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

A chromosomal loci of 11q22 has been inferred for ASP2 by homology (99% in 210 nucleotides) with Genbank Locus G24698 (Human STS WI-14206).

Antibodies

The polypeptides of the invention or their fragments or analogs thereof, or cells expressing them can also be used as immunogens to produce antibodies immunospecific for the ASP2 polypeptides. The term "immunospecific" means that the antibodies have substantially greater affinity for the polypeptides of the invention than their affinity for other related polypeptides in the prior art.

Antibodies generated against the ASP2 polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., *Nature* (1975) 256:495–497), the trioma technique, the human B-cell hybridoma technique (Kozbor et al., *Immunology Today* (1983) 4:72) and the EBV-hybridoma technique (Cole et al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against ASP2 polypeptides may also be employed to treat Alzheimer's Disease, cancer, and prohormone processing, among others.

Vaccines

Another aspect of the invention relates to a method for inducing an immunological response in a mammal which comprises inoculating the mammal with ASP2 polypeptide, or a fragment thereof, adequate to produce antibody and/or T cell immune response to protect said animal from Alzheimer's Disease, cancer, and prohormone processing, among others. Yet another aspect of the invention relates to a method of inducing immunological response in a mammal which comprises, delivering ASP2 polypeptide via a vector directing expression of ASP2 polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a ASP2 polypeptide wherein the composition comprises a ASP2 polypeptide or ASP2 gene. The vaccine formulation may further comprise a suitable carrier. Since ASP2 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The ASP2 polypeptide of the present invention may be employed in a screening process for compounds which activate (agonists) or inhibit activation of (antagonists, or otherwise called inhibitors) the ASP2 polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetic of the polypeptide of the present invention. See Coligan et al., *Current Protocols in Immunology* 1(2):Chapter5 (1991).

ASP2 polypeptides are responsible for many biological functions, including many pathologies. Accordingly, it is desirous to find compounds and drugs which stimulate ASP2 polypeptide on the one hand and which can inhibit the function of ASP2 polypeptide on the other hand. In general, agonists are employed for therapeutic and prophylactic purposes for such conditions as Alzheimer's Disease, cancer, and prohormone processing. Antagonists may be employed for a variety of therapeutic and prophylactic purposes for such conditions as Alzheimer's Disease, cancer, and prohormone processing.

In general, such screening procedures may involve using appropriate cells which express the ASP2 polypeptide or respond to ASP2 polypeptide of the present invention. Such cells include cells from mammals, yeast, Drosophila or *E coli*. Cells which express the ASP2 polypeptide (or cell membrane containing the expressed polypeptide) or respond to ASP2 polypeptide are then contacted with a test compound to observe binding, or stimulation or inhibition of a functional response. The ability of the cells which were contacted with the candidate compounds is compared with the same cells which were not contacted for ASP2 activity.

In addition, all aspartic proteinases are inhibited by pepstatin. Therefore, pepstatin inhibitory assays may also be employed with the present invention as a method of detection or as a screening assay.

The assays may simply test binding of a candidate compound wherein adherence to the cells bearing the ASP2 polypeptide is detected by means of a label directly or indirectly associated with the candidate compound or in an assay involving competition with a labeled competitor. Further, these assays may test whether the candidate compound results in a signal generated by activation of the ASP2 polypeptide, using detection systems appropriate to the cells bearing the ASP2 polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a ASP2 polypeptide to form a mixture, measuring ASP2 activity in the mixture, and comparing the ASP2 activity of the mixture to a standard.

The ASP2 cDNA, protein and antibodies to the protein may also be used to configure assays for detecting the effect of added compounds on the production of ASP2 mRNA and protein in cells. For example, an ELISA may be constructed for measuring secreted or cell associated levels of ASP2 protein using monoclonal and polyclonal antibodies by standard methods known in the art, and this can be used to discover agents which may inhibit or enhance the production of ASP2 (also called antagonist or agonist, respectively) from suitably manipulated cells or tissues.

The ASP2 protein may be used to identify membrane bound or soluble receptors, if any, through standard receptor binding techniques known in the art. These include, but are not limited to, ligand binding and crosslinking assays in which the ASP2 is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of ASP2 which compete with the binding of ASP2 to its receptors, if any. Standard methods for conducting screening assays are well understood in the art.

Examples of potential ASP2 polypeptide antagonists include antibodies or, in some cases, oligonucleotides or proteins which are closely related to the ligands, substrates, enzymes, receptors, etc., as the case may be, of the ASP2 polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for ASP2 polypeptides; or compounds which decrease or enhance the production of ASP2 polypeptides, which comprises:

(a) a ASP2 polypeptide, preferably that of SEQ ID NO:2;
(b) a recombinant cell expressing a ASP2 polypeptide, preferably that of SEQ ID NO:2;
(c) a cell membrane expressing a ASP2 polypeptide; preferably that of SEQ ID NO: 2; or
(d) antibody to a ASP2 polypeptide, preferably that of SEQ ID NO: 2.

It will be appreciated that in any such kit, (a), (b), (c) or (d) may comprise a substantial component.

Prophylactic and Therapeutic Methods

This invention provides methods of treating abnormal conditions such as, Alzheimer's Disease, cancer, and prohon-none processing, related to both an excess of and insufficient amounts of ASP2 polypeptide activity.

If the activity of ASP2 polypeptide is in excess, several approaches are available. One approach comprises administering to a subject an inhibitor compound (antagonist) as hereinabove described along with a pharmaceutically acceptable carrier in an amount effective to inhibit the function of the ASP2 polypeptide, such as, for example, by blocking the binding of ligands, substrates, enzymes, receptors, etc., or by inhibiting a second signal, and thereby alleviating the abnormal condition. In another approach, soluble forms of ASP2 polypeptides still capable of binding the ligand, substrate, enzymes, receptors, etc. in competition with endogenous ASP2 polypeptide may be administered. Typical embodiments of such competitors comprise fragments of the ASP2 polypeptide.

In another approach, soluble forms of ASP2 polypeptides still capable of binding the ligand in competition with endogenous ASP2 polypeptide may be administered. Typical embodiments of such competitors comprise fragments of the ASP2 polypeptide.

In still another approach, expression of the gene encoding endogenous ASP2 polypeptide can be inhibited using expression blocking techniques. Known such techniques involve the use of antisense sequences, either internally generated or separately administered. See, for example, O'Connor, *J Neurochem* (1991) 56:560 in *Oligodeoxynucleotides as Antisense Inhibitors of Gene Expression,* CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988)241:456; Dervan et al., *Science* (1991)251:1360. These oligomers can be administered per se or the relevant oligomers can be expressed in vivo.

For treating abnormal conditions related to an underexpression of ASP2 and its activity, several approaches are also available. One approach comprises administering to a subject a therapeutically effective amount of a compound which activates ASP2 polypeptide, i.e., an agonist as described above, in combination with a pharmaceutically acceptable carrier, to thereby alleviate the abnormal condition. Alternatively, gene therapy may be employed to effect the endogenous production of ASP2 by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches,* (and references cited therein) in Human Molecular Genetics, T Strachan and A P Read, BIOS Scientific Publishers Ltd (1996). Another approach is to administer a therapeutic amount of ASP2 polypeptides in combination with a suitable pharmaceutical carrier.

Formulation and Administration

Peptides, such as the soluble form of ASP2 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 $\mu$g/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

EXAMPLES

The examples below are carried out using standard techniques, which are well known and routine to those of skill in the art, except where otherwise described in detail. The examples illustrate, but do not limit the invention.

Cloning

Rapid amplification of cDNA ends polymerase chain reaction technology (RACE PCR) was used to identify the missing 5' cDNA sequence of the aspartyl protease 2 gene. The source of cDNA template for the amplification reactions was a range of Marathon-Ready™ cDNA preparations (Clontech Laboratories, Inc., 1020 East Meadow Circle, Palo Alto, Calif. 94303-4230, USA.). These Marathon-Ready cDNAs are essentially cDNA libraries which have oligonucleotide adaptors ligated onto them. This allows the researcher to perform 5' RACE PCR using two primers, one complementary to a region of known sequence in the gene of interest and the other complementary to the ligated adaptor; resulting in an extension to the known sequence at the 5' end. PCR was performed using AmpliTaq® Gold DNA polymerase (Perkin-Elmer Corp). It was found to be necessary to include 5% Dimethylsulphoxide in the reaction buffer for successful amplification, probably due to the high GC nucleotide content of this region of DNA.

The DNA sequence was cloned and a region of DNA was confirmed (nucleotides 1–273 in Table 1) at the 5' end of the Asp2 gene as extending from the start codon to overlap with the previously identified EST sequences. This novel sequence was identified in cDNA templates from seven human tissues, heart, leukocyte, mammary gland, spleen, skeletal muscle, thymus and aorta.

Northern Analysis

A human Multiple Tissue Northern blot (MTN catalogue number 7760-1) (Clontech) was hybridized with an Asp-2 specific probe (of 325 nuclcotides in length) generated by PCR, using the specific oligonucleotides 5' GATGAGTTCAGGACGGCAG 3' (SEQ ID NO:5) and 5' GGTGCCATATGTGTCTCC 3' (SEQ ID NO:6). The probe was radiolabelled by incorporation of $^{32}$P-dCTP during PCR amplification, and the labelled PCR product was subsequently purified using the Qiagen PCR Purification Kit. After a 1hour prehybridization, hybridization was carried out for 2 hours using ExpressHyb buffer (Clontcch) at 68° C., and the labelled probe was added to a final concentration of $1\times10^6$ cpm/ml. After hybridization, the membrane was washed twice in 2×SSC/0.05% SDS for 20 minutes, and twice in 0.1×SSC/0.1% SDS at 50° C. for 20 minutes. The membrane was then wrapped in plastic wrap and exposed to X-ray film at −70° C. with two intensifying screens. This revealed that the highest expression (tissues examined were heart, brain, placenta, lung, liver, skeletal muscle, kidney and pancreas) of Asp2 was in the pancreas, followed by the brain.

All publications, including but not limited to patents and patent applications, cited in this specification are herein incorporated by reference as if each individual publication Were specifically and individually indicated to be incorporated by reference herein as though fully set forth.

What is claimed is:

1. An isolated polynucleotide comprising a nucleotide sequence which, by virtue of degeneracy of the genetic code, encodes the amino acid sequence set forth in SEQ ID NO:2.

2. An isolated polynucleotide comprising the nucleotide sequence set forth in SEQ ID NO: 1.

3. An isolated polynucleotide consisting of the polynucleotide sequence set forth in SEQ ID NO: 1.

4. The isolated polynucleotide of claim 1 which is DNA.

5. An expression vector comprising an isolated polynucleotide, wherein said expression vector produces an ASP2 polypeptide comprising the amino acid sequence set forth in SEQ ID NO:2 when said expression vector is present in a compatible host cell.

6. A recombinant host cell comprising the expression vector of claim 5.

7. A process for producing an ASP2 polypeptide comprising culturing the recombinant host cell of claim 6 under conditions sufficient for the production of said polypeptide and recovering the polypeptide from the culture.

8. A process for producing a cell which produces an ASP2 polypeptide thereof comprising transforming or transfecting a host cell with the expression vector of claim 5 such that the host cell, under appropriate culture conditions, produces an ASP2 polypeptide.

9. A recombinant host cell produced by a method of claim 8 or an isolated membrane fraction thereof expressing an ASP2 polypeptide.

10. An isolated polynucleotide that is fully complementary to a nucleotide sequence selected from the group consisting of:

(a) a nucleotide sequence which, by virtue of degeneracy of the genetic code, encodes the amino acid sequence set forth in SEQ ID NO:2;

(b) a nucleotide sequence comprising SEQ ID NO:1; and (c) a nucleotide sequence consisting of SEQ ID NO:1.

11. The isolated polynucleotide of claim 1 which is RNA.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 2541 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

| | | | | | | |
|---|---|---|---|---|---|---|
| ATGGCCCAAG | CCCTGCCCTG | GCTCCTGCTG | TGGATGGGCG | CGGGAGTGCT | GCCTGCCCAC | 60 |
| GGCACCCAGC | ACGGCATCCG | GCTGCCCCTG | CGCAGCGGCC | TGGGGGGCGC | CCCCCTGGGG | 120 |
| CTGCGGCTGC | CCCGGGAGAC | CGACGAAGAG | CCCGAGGAGC | CCGGCCGGAG | GGGCAGCTTT | 180 |
| GTGGAGATGG | TGGACAACCT | GAGGGGCAAG | TCGGGGCAGG | GCTACTACGT | GGAGATGACC | 240 |
| GTGGGCAGCC | CCCCGCAGAC | GCTCAACATC | CTGGTGGATA | CAGGCAGCAG | TAACTTTGCA | 300 |
| GTGGGTGCTG | CCCCCCACCC | CTTCCTGCAT | CGCTACTACC | AGAGGCAGCT | GTCCAGCACA | 360 |
| TACCGGGACC | TCCGGAAGGG | TGTGTATGAG | CCCTACACCC | AGGGCAAGTG | GGAAGGGGAG | 420 |
| CTGGGCACCG | ACCTGGTAAG | CATCCCCCAT | GGCCCCAACG | TCACTGTGCG | TGCCAACATT | 480 |

```
GCTGCCATCA CTGAATCAGA CAAGTTCTTC ATCAACGGCT CCAACTGGGA AGGCATCCTG    540

GGGCTGGCCT ATGCTGAGAT TGCCAGGCCT GACGACTCCC TGGAGCCTTT CTTTGACTCT    600

CTGGTAAAGC AGACCCACGT TCCCAACCTC TTCTCCCTGC AGCTTTGTGG TGCTGGCTTC    660

CCCCTCAACC AGTCTGAAGT GCTGGCCTCT GTCGGAGGGA GCATGATCAT TGGAGGTATC    720

GACCACTCGC TGTACACAGG CAGTCTCTGG TATACACCCA TCCGGCGGGA GTGGTATTAT    780

GAGGTGATCA TTGTGCGGGT GGAGATCAAT GGACAGGATC TGAAAATGGA CTGCAAGGAG    840

TACAACTATG ACAAGAGCAT TGTGGACAGT GGCACCACCA ACCTTCGTTT GCCCAAGAAA    900

GTGTTTGAAG CTGCAGTCAA ATCCATCAAG GCAGCCTCCT CCACGGAGAA GTTCCCTGAT    960

GGTTTCTGGC TAGGAGAGCA GCTGGTGTGC TGGCAAGCAG GCACCACCCC TTGGAACATT   1020

TTCCCAGTCA TCTCACTCTA CCTAATGGGT GAGGTTACCA ACCAGTCCTT CCGCATCACC   1080

ATCCTTCCGC AGCAATACCT GCGGCCAGTG GAAGATGTGG CCACGTCCCA AGACGACTGT   1140

TACAAGTTTG CCATCTCACA GTCATCCACG GGCACTGTTA TGGGAGCTGT TATCATGGAG   1200

GGCTTCTACG TTGTCTTTGA TCGGGCCCGA AAACGAATTG CTTTGCTGT CAGCGCTTGC   1260

CATGTGCACG ATGAGTTCAG GACGGCAGCG GTGGAAGGCC CTTTTGTCAC CTTGGACATG   1320

GAAGACTGTG GCTACAACAT TCCACAGACA GATGAGTCAA CCCTCATGAC CATAGCCTAT   1380

GTCATGGCTG CCATCTGCGC CCTCTTCATG CTGCCACTCT GCCTCATGGT GTGTCAGTGG   1440

CGCTGCCTCC GCTGCCTGCG CCAGCAGCAT GATGACTTTG CTGATGACAT CTCCCTGCTG   1500

AAGTGAGGAG GCCCATGGGA GAAAGATAGA GATTCCCCTG GGACCACACC TCCGTGGTTC   1560

ACTTTGGTCA CAAGTAGGAG ACACAGATGG CACCTGTGGC CAGAGCACCT CAGGACCCTC   1620

CCCACCCACC AAATGCCTCT GCCTTGATGG AGAAGGAAAA GGCTGGCAAG GTGGGTTCCA   1680

GGGACTGTAC CTGTAGGAAA CAGAAAAGAG AAGAAAGAAG CACTCTGCTG GCGGGAATAC   1740

TCTTGGTCAC CTCAAATTTA AGTCGGGAAA TTCTGCTGCT TGAAACTTCA GCCCTGAACC   1800

TTTGTCCACC ATTCCTTTAA ATTCTCCAAC CCAAAGTATT CTTCTTTTCT TAGTTTCAGA   1860

AGTACTGGCA TCACACGCAG GTTACCTTGG CGTGTGTCCC TGTGGTACCC GGGCAGAGAA   1920

GAGACCAAGC TTGTTTCCCT GCTGGCCAAA GTCAGTAGGA GAGGATGCAC AGTTTGCTAT   1980

TTGCTTTAGA GACAGGGACT GTATAAACAA GCCTAACATT GGTGCAAAGA TTGCCTCTTG   2040

AATTAAAAAA AAAAACTAGA TTGACTATTT ATACAAATGG GGGCGGCTGG AAAGAGGAGA   2100

AGGAGAGGGA GTACAAAGAC AGGGAATAGT GGGATCAAAG CTAGGAAAGG CAGAAACACA   2160

ACCACTCACC AGTCCTAGTT TTAGACCTCA TCTCCAAGAT AGCATCCCAT CTCAGAAGAT   2220

GGGTGTTGTT TTCAATGTTT TCTTTTCTGT GGTTGCAGCC TGACCAAAAG TGAGATGGGA   2280

AGGGCTTATC TAGCCAAAGA GCTCTTTTTT AGCTCTCTTA AATGAAGTGC CCACTAAGGA   2340

AGTTCCACTT GAACACATGG AATTTCTGCC ATATTAATTT CCATTGTCTC TATCTGGAAC   2400

CACCCTTTAA TCTCTACATA TGATTAGGTC CAGCACTTGA AAATATTCCT AACCNNAATT   2460

TGNCTTGGGG GCTTTGCNGN CCAGGTGCTA AAAGGGNTTG GGTAGGNGNC CNCTTNTATN   2520

TNATNCCTNA AAAGGTTANN G                                             2541
```

(2) INFORMATION FOR SEQ ID NO:2:

(i) SEQUENCE CHARACTERISTICS:
        (A) LENGTH: 501 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Ala Gln Ala Leu Pro Trp Leu Leu Leu Trp Met Gly Ala Gly Val
 1               5                  10                  15

Leu Pro Ala His Gly Thr Gln His Gly Ile Arg Leu Pro Leu Arg Ser
             20                  25                  30

Gly Leu Gly Gly Ala Pro Leu Gly Leu Arg Leu Pro Arg Glu Thr Asp
         35                  40                  45

Glu Glu Pro Glu Glu Pro Gly Arg Arg Gly Ser Phe Val Glu Met Val
 50                  55                  60

Asp Asn Leu Arg Gly Lys Ser Gly Gln Gly Tyr Tyr Val Glu Met Thr
 65                  70                  75                  80

Val Gly Ser Pro Pro Gln Thr Leu Asn Ile Leu Val Asp Thr Gly Ser
                 85                  90                  95

Ser Asn Phe Ala Val Gly Ala Ala Pro His Pro Phe Leu His Arg Tyr
             100                 105                 110

Tyr Gln Arg Gln Leu Ser Ser Thr Tyr Arg Asp Leu Arg Lys Gly Val
         115                 120                 125

Tyr Glu Pro Tyr Thr Gln Gly Lys Trp Glu Gly Glu Leu Gly Thr Asp
 130                 135                 140

Leu Val Ser Ile Pro His Gly Pro Asn Val Thr Val Arg Ala Asn Ile
 145                 150                 155                 160

Ala Ala Ile Thr Glu Ser Asp Lys Phe Phe Ile Asn Gly Ser Asn Trp
                 165                 170                 175

Glu Gly Ile Leu Gly Leu Ala Tyr Ala Glu Ile Ala Arg Pro Asp Asp
             180                 185                 190

Ser Leu Glu Pro Phe Phe Asp Ser Leu Val Lys Gln Thr His Val Pro
         195                 200                 205

Asn Leu Phe Ser Leu Gln Leu Cys Gly Ala Gly Phe Pro Leu Asn Gln
 210                 215                 220

Ser Glu Val Leu Ala Ser Val Gly Gly Ser Met Ile Ile Gly Gly Ile
 225                 230                 235                 240

Asp His Ser Leu Tyr Thr Gly Ser Leu Trp Tyr Thr Pro Ile Arg Arg
                 245                 250                 255

Glu Trp Tyr Tyr Glu Val Ile Ile Val Arg Val Glu Ile Asn Gly Gln
             260                 265                 270

Asp Leu Lys Met Asp Cys Lys Glu Tyr Asn Tyr Asp Lys Ser Ile Val
         275                 280                 285

Asp Ser Gly Thr Thr Asn Leu Arg Leu Pro Lys Lys Val Phe Glu Ala
 290                 295                 300

Ala Val Lys Ser Ile Lys Ala Ala Ser Ser Thr Glu Lys Phe Pro Asp
 305                 310                 315                 320

Gly Phe Trp Leu Gly Glu Gln Leu Val Cys Trp Gln Ala Gly Thr Thr
             325                 330                 335

Pro Trp Asn Ile Phe Pro Val Ile Ser Leu Tyr Leu Met Gly Glu Val
         340                 345                 350

Thr Asn Gln Ser Phe Arg Ile Thr Ile Leu Pro Gln Gln Tyr Leu Arg
 355                 360                 365

Pro Val Glu Asp Val Ala Thr Ser Gln Asp Asp Cys Tyr Lys Phe Ala
 370                 375                 380

Ile Ser Gln Ser Ser Thr Gly Thr Val Met Gly Ala Val Ile Met Glu
 385                 390                 395                 400
```

-continued

```
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
                420                 425                 430
Gly Pro Phe Val Thr Leu Asp Met Glu Asp Cys Gly Tyr Asn Ile Pro
                435                 440                 445
Gln Thr Asp Glu Ser Thr Leu Met Thr Ile Ala Tyr Val Met Ala Ala
            450                 455                 460
Ile Cys Ala Leu Phe Met Leu Pro Leu Cys Leu Met Val Cys Gln Trp
465                 470                 475                 480
Arg Cys Leu Arg Cys Leu Arg Gln Gln His Asp Asp Phe Ala Asp Asp
                485                 490                 495
Ile Ser Leu Leu Lys
            500
```

(2) INFORMATION FOR SEQ ID NO:3:

(i) SEQUENCE CHARACTERISTICS:
        (A) LENGTH: 2370 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GGCAGCTTTG TGGAGATGGT GGACAACCTG AGGGGCAAGT CGGGGCAGGG CTACTACGTG     60
GAGATGACCG TGGGCAGCCC CCCGCAGACG CTCAACATCC TGGTGGATAC AGGCAGCAGT    120
AACTTTGCAG TGGGTGCTGC CCCCCACCCC TTCCTGCATC GCTACTACCA GAGGCAGCTG    180
TCCAGCACAT ACCGGGACCT CCGGAAGGGT GTGTATGAGC CCTACACCCA GGGCAAGTGG    240
GAAGGGGAGC TGGGCACCGA CCTGGTAAGC ATCCCCCATG GCCCCAACGT CACTGTGCGT    300
GCCAACATTG CTGCCATCAC TGAATCAGAC AAGTTCTTCA TCAACGGCTC CAACTGGGAA    360
GGCATCCTGG GCTGGCCTA TGCTGAGATT GCCAGGCCTG ACGACTCCCT GGAGCCTTTC    420
TTTGACTCTC TGGTAAAGCA GACCCACGTT CCCAACCTCT TCTCCCTGCA GCTTTGTGGT    480
GCTGGCTTCC CCCTCAACCA GTCTGAAGTG CTGGCCTCTG TCGGAGGGAG CATGATCATT    540
GGAGGTATCG ACCACTCGCT GTACACAGGC AGTCTCTGGT ATACACCCAT CCGGCGGGAG    600
TGGTATTATG AGGTGATCAT TGTGCGGGTG GAGATCAATG ACAGGATCT GAAAATGGAC    660
TGCAAGGAGT ACAACTATGA CAAGAGCATT GTGGACAGTG GCACCACCAA CCTTCGTTTG    720
CCCAAGAAAG TGTTTGAAGC TGCAGTCAAA TCCATCAAGG CAGCCTCTCC ACGGGAGAAG    780
TTCCCTGATG GTTTCTGGCT AGGAGAGCAG CTGGTGTGCT GGCAAGCAGG CACCACCCCT    840
TGGAACATTT TCCCAGTCAT CTCACTCTAC CTAATGGGTG AGGTTACCAA CCAGTCCTTC    900
CGCATCACCA TCCTTCCGCA GCAATACCTG CGGCCAGTGG AAGATGTGGC CACGTCCCAA    960
GACGACTGTT ACAAGTTTGC CATCTCACAG TCATCCACGG GCACTGTTAT GGGAGCTGTT   1020
ATCATGGAGG GCTTCTACGT TGTCTTTGAT CGGGCCCGAA AACGAATTGG CTTTGCTGTC   1080
AGCGCTTGCC ATGTGCACGA TGAGTTCAGG ACGGCAGCGG TGGAAGGCCC TTTTGTCACC   1140
TTGGACATGG AAGACTGTGG CTACAACATT CCACAGACAG ATGAGTCAAC CCTCATGACC   1200
ATAGCCTATG TCATGGCTGC CATCTGCGCC CTCTTCATGC TGCCACTCTG CCTCATGGTG   1260
TGTCAGTGGC GCTGCCTCCG CTGCCTGCGC CAGACAATGG ATGACTTTGC TGATGACATC   1320
TCCCTGCTGA AGTGAGGAGG CCCATGGGAG AAAGATAGAG ATTCCCCTGG GACCACACCT   1380
```

```
CCGTGGTTCA CTTTGGTCAC AAGTAGGAGA CACAGATGGC ACCTGTGGCC AGAGCACCTC    1440

AGGACCCTCC CCACCCACCA AATGCCTCTG CCTTGATGGA GAAGGAAAAG GCTGGCAAGG    1500

TGGGTTCCAG GGACTGTACC TGTAGGAAAC AGAAAAGAGA AGAAAGAAGC ACTCTGCTGG    1560

CGGGAATACT CTTGGTCACC TCAAATTTAA GTCGGGAAAT TCTGCTGCTT GAAACTTCAG    1620

CCCTGAACCT TTGTCCACCA TTCCTTTAAA TTCTCCAACC CAAAGTATTC TTCTTTTCTT    1680

AGTTTCAGAA GTACTGGCAT CACACGCAGG TTACCTTGGC GTGTGTCCCT GTGGTACCCG    1740

GGCAGAGAAG AGACCAAGCT TGTTTCCCTG CTGGCCAAAG TCAGTAGGAG AGGATGCACA    1800

GTTTGCTATT TGCTTTAGAG ACAGGGACTG TATAAACAAG CCTAACATTG GTGCAAAGAT    1860

TGCCTCTTGA ATTAAAAAAA AAAACTAGAT TGACTATTTA TACAAATGGG GGCGGCTGGA    1920

AAGAGGAGAA GGAGAGGGAG TACAAAGACA GGGAATAGTG GGATCAAAGC TAGGAAAGGC    1980

AGAAACACAA CCACTCACCA GTCCTAGTTT TAGACCTCAT CTCCAAGATA GCATCCCATC    2040

TCAGAAGATG GGTGTTGTTT TCAATGTTTT CTTTTCTGTG GTTGCAGCCT GACCAAAAGT    2100

GAGATGGGAA GGGCTTATCT AGCCAAAGAG CTCTTTTTTA GCTCTCTTAA ATGAAGTGCC    2160

CACTAAGGAA GTTCCACTTG AACACATGGA ATTTCTGCCA TATTAATTTC CATTGTCTCT    2220

ATCTGGAACC ACCCTTTAAT CTCTACATAT GATTAGGTCC AGCACTTGAA AATATTCCTA    2280

ACCNNAATTT GNCTTGGGGG CTTTGCNGNC CAGGTGCTAA AAGGGNTTGG GTAGGNGNCC    2340

NCTTNTATNT NATNCCTNAA AAGGTTANNG                                    2370

(2) INFORMATION FOR SEQ ID NO:4:

(i) SEQUENCE CHARACTERISTICS:
        (A) LENGTH: 774 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Gly Ser Phe Val Glu Met Val Asp Asn Leu Arg Gly Lys Ser Gly Gln
 1               5                  10                  15

Gly Tyr Tyr Val Glu Met Thr Val Gly Ser Pro Gln Thr Leu Asn
            20                  25                  30

Ile Leu Val Asp Thr Gly Ser Ser Asn Phe Ala Val Gly Ala Ala Pro
            35                  40                  45

His Pro Phe Leu His Arg Tyr Tyr Gln Arg Gln Leu Ser Ser Thr Tyr
 50                  55                  60

Arg Asp Leu Arg Lys Gly Val Tyr Glu Pro Tyr Thr Gln Gly Lys Trp
 65                  70                  75                  80

Glu Gly Glu Leu Gly Thr Asp Leu Val Ser Ile Pro His Gly Pro Asn
                85                  90                  95

Val Thr Val Arg Ala Asn Ile Ala Ala Ile Thr Glu Ser Asp Lys Phe
            100                 105                 110

Phe Ile Asn Gly Ser Asn Trp Glu Gly Ile Leu Gly Leu Ala Tyr Ala
            115                 120                 125

Glu Ile Ala Arg Pro Asp Asp Ser Leu Glu Pro Phe Phe Asp Ser Leu
    130                 135                 140

Val Lys Gln Thr His Val Pro Asn Leu Phe Ser Leu Gln Leu Cys Gly
145                 150                 155                 160

Ala Gly Phe Pro Leu Asn Gln Ser Glu Val Leu Ala Ser Val Gly Gly
```

```
              165                 170                 175
Ser Met Ile Ile Gly Gly Ile Asp His Ser Leu Tyr Thr Gly Ser Leu
            180                 185                 190

Trp Tyr Thr Pro Ile Arg Arg Glu Trp Tyr Tyr Glu Val Ile Ile Val
            195                 200                 205

Arg Val Glu Ile Asn Gly Gln Asp Leu Lys Met Asp Cys Lys Glu Tyr
            210                 215                 220

Asn Tyr Asp Lys Ser Ile Val Asp Ser Gly Thr Thr Asn Leu Arg Leu
225                 230                 235                 240

Pro Lys Lys Val Phe Glu Ala Ala Val Lys Ser Ile Lys Ala Ala Ser
                245                 250                 255

Pro Arg Glu Lys Phe Pro Asp Gly Phe Trp Leu Gly Glu Gln Leu Val
            260                 265                 270

Cys Trp Gln Ala Gly Thr Thr Pro Trp Asn Ile Phe Pro Val Ile Ser
            275                 280                 285

Leu Tyr Leu Met Gly Glu Val Thr Asn Gln Ser Phe Arg Ile Thr Ile
            290                 295                 300

Leu Pro Gln Gln Tyr Leu Arg Pro Val Glu Asp Val Ala Thr Ser Gln
305                 310                 315                 320

Asp Asp Cys Tyr Lys Phe Ala Ile Ser Gln Ser Ser Thr Gly Thr Val
                325                 330                 335

Met Gly Ala Val Ile Met Glu Gly Phe Tyr Val Val Phe Asp Arg Ala
            340                 345                 350

Arg Lys Arg Ile Gly Phe Ala Val Ser Ala Cys His Val His Asp Glu
            355                 360                 365

Phe Arg Thr Ala Ala Val Glu Gly Pro Phe Val Thr Leu Asp Met Glu
            370                 375                 380

Asp Cys Gly Tyr Asn Ile Pro Gln Thr Asp Glu Ser Thr Leu Met Thr
385                 390                 395                 400

Ile Ala Tyr Val Met Ala Ala Ile Cys Ala Leu Phe Met Leu Pro Leu
                405                 410                 415

Cys Leu Met Val Cys Gln Trp Arg Cys Leu Arg Cys Leu Arg Gln Thr
            420                 425                 430

Met Asp Asp Phe Ala Asp Asp Ile Ser Leu Leu Lys Gly Gly Pro Trp
            435                 440                 445

Glu Lys Asp Arg Asp Ser Pro Gly Thr Thr Pro Pro Trp Phe Thr Leu
450                 455                 460

Val Thr Ser Arg Arg His Arg Trp His Leu Trp Pro Glu His Leu Arg
465                 470                 475                 480

Thr Leu Pro Thr His Gln Met Pro Leu Pro Trp Arg Arg Lys Arg Leu
                485                 490                 495

Ala Arg Trp Val Pro Gly Thr Val Pro Val Gly Asn Arg Lys Glu Lys
            500                 505                 510

Lys Glu Ala Leu Cys Trp Arg Glu Tyr Ser Trp Ser Pro Gln Ile Val
            515                 520                 525

Gly Lys Phe Cys Cys Leu Lys Leu Gln Pro Thr Phe Val His His Ser
            530                 535                 540

Phe Lys Phe Ser Asn Pro Lys Tyr Ser Ser Phe Leu Ser Phe Arg Ser
545                 550                 555                 560

Thr Gly Ile Thr Arg Arg Leu Pro Trp Arg Val Ser Leu Trp Tyr Pro
                565                 570                 575

Gly Arg Glu Glu Thr Lys Leu Val Ser Leu Leu Ala Lys Val Ser Arg
            580                 585                 590
```

-continued

```
Arg Gly Cys Thr Val Cys Tyr Leu Leu Arg Gln Gly Leu Tyr Lys Gln
        595                 600                 605
Ala His Trp Cys Lys Asp Cys Leu Leu Asn Lys Lys Lys Leu Asp Leu
        610                 615                 620
Phe Ile Gln Met Gly Ala Ala Gly Lys Arg Arg Arg Arg Gly Ser Thr
625                 630                 635                 640
Lys Thr Gly Asn Ser Gly Ile Lys Ala Arg Lys Gly Arg Asn Thr Thr
                645                 650                 655
Thr His Gln Ser Phe Thr Ser Ser Pro Arg His Pro Ile Ser Glu Asp
                660                 665                 670
Gly Cys Cys Phe Gln Cys Phe Leu Phe Cys Gly Cys Ser Leu Thr Lys
        675                 680                 685
Ser Glu Met Gly Arg Ala Tyr Leu Ala Lys Glu Leu Phe Phe Ser Ser
        690                 695                 700
Leu Lys Ser Ala His Gly Ser Ser Thr Thr His Gly Ile Ser Ala Ile
705                 710                 715                 720
Leu Ile Ser Ile Val Ser Ile Trp Asn His Pro Leu Ile Ser Thr Tyr
                725                 730                 735
Asp Val Gln His Leu Lys Ile Phe Leu Thr Xaa Ile Xaa Leu Gly Gly
                740                 745                 750
Phe Ala Xaa Gln Val Leu Lys Gly Xaa Gly Xaa Xaa Xaa Xaa Xaa
        755                 760                 765
Xaa Leu Lys Arg Leu Xaa
    770
```

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GATGAGTTCA GGACGGCAG                                        19

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGTGCCATAT GTGTCTCC                                         18